United States Patent
Brulez et al.

(10) Patent No.: US 11,351,288 B2
(45) Date of Patent: Jun. 7, 2022

(54) RESORBABLE BIOMIMETIC PROSTHETIC LIGAMENT

(71) Applicant: L.A.R.S.—LABORATOIRE D'APPLICATION ET DE RECHERCHE SCIENTIFIQUE, Arc sur Tille (FR)

(72) Inventors: Bernard Brulez, Bourbonne les Bains (FR); Véronique Migonney, Eaubonne (FR); Roger Guilard, Fontaine les Dijon (FR)

(73) Assignee: L.A.R.S.—LABORATOIRE D'APPLICATION ET DE RECHERCHE SCIENTIFIQUE, Arc sur Tille (FR)

( * ) Notice: Subject to any disclaimer, the term of this patent is extended or adjusted under 35 U.S.C. 154(b) by 397 days.

(21) Appl. No.: 15/038,259

(22) PCT Filed: Nov. 21, 2014

(86) PCT No.: PCT/FR2014/052992
§ 371 (c)(1),
(2) Date: May 20, 2016

(87) PCT Pub. No.: WO2015/075397
PCT Pub. Date: May 28, 2015

(65) Prior Publication Data
US 2016/0287746 A1  Oct. 6, 2016

(30) Foreign Application Priority Data
Nov. 22, 2013 (FR) ........................ 1361522

(51) Int. Cl.
| | |
|---|---|
| *A61L 27/16* | (2006.01) |
| *A61L 27/18* | (2006.01) |
| *A61F 2/08* | (2006.01) |
| *A61L 27/22* | (2006.01) |
| *A61L 27/24* | (2006.01) |
| *A61L 27/54* | (2006.01) |
| *A61L 27/58* | (2006.01) |

(52) U.S. Cl.
CPC ................ *A61L 27/16* (2013.01); *A61F 2/08* (2013.01); *A61L 27/18* (2013.01); *A61L 27/227* (2013.01); *A61L 27/24* (2013.01); *A61L 27/54* (2013.01); *A61L 27/58* (2013.01); *A61F 2210/0004* (2013.01); *A61F 2240/001* (2013.01); *A61L 2300/21* (2013.01); *A61L 2300/252* (2013.01); *A61L 2400/18* (2013.01); *A61L 2430/10* (2013.01)

(58) Field of Classification Search
CPC ................ A61F 2/08; A61F 2210/0004; A61F 2240/001; A61L 27/16; A61L 27/18; A61L 27/227; A61L 27/24; A61L 27/54; A61L 27/58; A61L 2300/21; A61L 2300/252; A61L 2400/18; A61L 2430/10
See application file for complete search history.

(56) References Cited

U.S. PATENT DOCUMENTS

| | | | | |
|---|---|---|---|---|
| 2006/0136057 A1* | 6/2006 | Brulez | .................... | A61L 27/18 623/13.11 |
| 2011/0238178 A1* | 9/2011 | Downes | .................. | A61L 27/18 623/13.11 |

FOREIGN PATENT DOCUMENTS

FR    2850026 A1    7/2004

OTHER PUBLICATIONS

Kint poly(ethylene terephthalate) 1999 Polym. Int. p. 346.*
Shao, poly (epsilon-caprolactone) 2009 J. Biomedical Mat. Res. Part A, p. 1298.*
Laurencin Anterior cruciate ligament regeneration Soft Matter p. 5016 (Year: 2010).*
Woodruff, Polymer-Polycaprolactone, Progress in Polym. Sci. p. 1217 (Year: 2010).*
International Search Report and Written opinion dated Mar. 10, 2015 in corresponding application No. PCT/FR2014/052992; 12 pgs.
International Preliminary Report dated Apr. 28, 2016 in corresponding application No. PCT/FR2014/052992; 16 pgs.
International Preliminary Report on Patentability issued in corresponding International Patent Application No. PCT/FR2014/052992 dated Jun. 23, 2016 (9 pgs., including English language translation).

* cited by examiner

*Primary Examiner* — Matthew P Coughlin
*Assistant Examiner* — Thurman Wheeler
(74) *Attorney, Agent, or Firm* — Maier & Maier, PLLC

(57) ABSTRACT

An artificial ligament prosthesis which is notable in that it comprises a layer totally or partly consisting of PCL fibres. The ligament prosthesis is a biodegradable and "biointegrable" artificial ligament which makes it possible to take away all the apprehensions and uncertainties due to non-degradable synthetic supports. It is a prosthetic structure inspired by and similar to the native tissue, which is biodegradable while being sterilisable. It can optionally be seeded in order to facilitate the formation of functional tissues with controlled cell and tissue activity, having the required mechanical properties. The prosthesis maybe slowly resorbable in order to be gradually replaced with a functional tissue identical to that of the native ligament.

17 Claims, No Drawings

RESORBABLE BIOMIMETIC PROSTHETIC LIGAMENT

TECHNICAL FIELD

This invention relates to a resorbable biomimetic prosthetic ligament as well as the method for obtaining it.

PRIOR ART

The anterior cruciate ligament (ACL) tearing of the knee is a common condition with an incidence evaluated at 1 per 3,000 inhabitants per year in the United States and in Europe. It occurs primarily in athletes: as such, the history of the tearing of the ACL begins in over 65% of the cases with a sports accident (ski, football, rugby, combat sports). The average age at the time of the accident is between 20 and 29 years old, and 70% of the patients afflicted are between 20 and 40 years old.

ACL is an essential element in the stabilisation of the knee. Once torn, due to the intra-articular location of it and the poor vascularisation of it, it does not heal spontaneously and it evolves into a retraction and degeneration of the torn ends. The slackness of the knee that results from this causes a functional impact with instability that will hinder or prevent the practice of sports activities and even everyday activities of life. Moreover, this slackness favours in the long run the occurrence of meniscus lesions then osteoarthritic degradation of the knee which is observed at the age of 30 years in 85% of the subjects afflicted (HAS report, June 2008). For all of these reasons, recourse to a surgical operation is frequent, in particular in young subjects. In France, 35,732 patients underwent a surgical operation in 2010, following a tearing of the ACL (Source PMSI 2010).

The usual surgical techniques are based on replacing the ACL with an autologous transplant: the patellar tendon (Kenneth Jones technique) or the tendons of the medial rectus and semitendinosus muscle (DIDT technique). The utilisation of an autograft is not however devoid of disadvantages (morbidity linked to tissue sampling, anchoring defect of the graft on the bone and tearing rate that is still too high with a failure rate estimated to be about 15%) and induces substantial recovery delays for resuming sports activities (>6 months).

The alternative consists in replacing the torn ligament with a synthetic ligament prosthesis which decreases the iatrogenicity of the surgical procedure and offers immediate mechanical support. This latter solution is proposed by certain surgeons to high-level athletes for whom the functional recovery has to be fast and to patients afflicted with multi-ligament injuries which are less frequent but more serious. In this latter case, the absence of transplants in a sufficient quantity can lead to the use of allografts that have a risk of viral transmission or to using, for the posterior cruciate ligament, a synthetic ligament prosthesis as a healing aid. There is also an economic interest for this use through the decrease in the indirect costs linked to the periods of functional rehabilitation and stoppage of activity.

The development of artificial ligaments in the years 1970-80 had for ambition to overcome the insufficiencies and complications linked to ligament autografts and allografts. Many artificial ligaments have been proposed, first made of carbon, then of poly(ethylene), poly(ethylene terephtalate) (Leeds-Keio ligament), poly(propylene) (Kennedy Ligament Augmentation Device), or poly(tetrafluoroethylene) (Gore-tex, or ABC Surgicraft). Although the results of these ligaments in the treating of ACL tearing were good in the short term, the choice of materials was entirely inadequate and because of this their low resistance to abrasion, their high rate of rupture in fatigue and their low integration naturally favoured the failures observed in the middle term. The production of ligament debris by fragmentation was the source of inflammatory synovitis and of definitive chondral lesions. The histological examination of the explanted ligaments has furthermore shown that the tissue colonisation was inhomogeneous and that it constituted more of a destructuring elements than a mechanical strengthening elements. After a phase of initial enthusiasm, the use of these ligaments therefore gradually became limited for use as a material for reinforcing an autologous ligament structure rather than as a genuine substitute. The poor results with these first ligaments resulted in a non-recommendation for them in the framework of ligamentoplasty as a first-line for anterior cruciate in France.

During the years 1990 to 2000, a 2nd generation of synthetic ligament was developed and made it possible to propose an innovative solution in this specific field (Ligaments LARS). The LARS prosthesis (artificial ligament made of PET) which constitutes via its innovative structure the second generation of ligament prostheses has been one of the mostly widely used artificial ligaments for about fifteen years. However, since no one today knows the long-term impact of the presence of a synthetic structure in the joint of the knee, third-generation artificial ligaments have also been proposed. These bioactive artificial ligaments that can be used without a hostile reaction of the host, described in patent FR0300495, make it possible to improve the tissue colonisation and functionality of the tissues and the bone anchoring.

In order to overcome these insufficiencies, this application proposes to develop a bioactive and biodegradable (biohybrid) ligament that does not have any of the defects of current ligaments and which constitutes a medical device that is easy to manipulate by the practitioner and which induces a genuine regeneration of the injured tissue.

SUMMARY OF THE INVENTION

As such this invention relates in particular to an artificial ligament prosthesis which is notable in that it comprises a layer totally or partly consisting of biodegradable fibres and advantageously of PCL.

According to a preferred embodiment of the invention, said artificial ligament is an articular or periarticular ligament. According to an entirely preferred embodiment, said artificial ligament is an anterior or posterior cruciate ligament.

Advantageously, said ligament prosthesis is constituted of said layer rolled or folded over itself, said layer comprises entirely advantageously two intra-osseous end portions and an intermediate intra-articular portion. Said intermediate portion is preferentially comprised of a web of longitudinal weft threads, adjacent and not connected together transversely. When the ligament is mounted, a longitudinal twist is given to each active thread, resulting in a dextrorotatory or a laevorotatory ligament that reproduces the natural twisting of ligaments in flexion.

In the framework of this invention, the term "biodegradable" refers to materials that can be broken down once in place in the organism. According to a preferred embodiment of the invention, the term "biodegradable" refers to fibres able to lose between 1 and 100% of their constituents in a period of exposure to physiological conditions between 1 month and 4 years. According to an entirely preferred embodiment of the invention the term biodegradable refers to the materials selected from the group comprising poly ε-caprolactone (PCL), copolymers of ε-caprolactone and of lactic acid (L and D) or of glycolic acids, copolymers of glycolic and lactic acids (L and D), polydioxanone, polyhydroxyalcanoate and copolymers of these various molecules.

Entirely advantageously, said biodegradable fibres are PCL fibres. This type of ligament made of PCL, a material of which the biocompatibility is well known, has an extremely high resistance to traction, flexion and torsion forces.

Polycaprolactone (PCL) was widely used in the 1970's and 1980's in the field of biodegradable suture threads, and use of it has slowly decreased to the benefit of more quickly resorbable polyesters, such as PLGA. PCL is a semi-crystalline polymer with a high degree of crystallinity (~50%) that has a glass transition temperature Tg of −60° C. and a melting temperature Tm of 60° C. As such, when used at 37° C., the macromolecular chains of PCL are in a highly "flexible" state allowing it to be used for the tissue engineering of soft tissues. Furthermore, use of it in the biomedical field has already been validated since a large number of drug delivery devices have received approval from the FDA and CE marking.

PCL breaks down slowly (up to 4 years according to the molar mass and the morphology of the material) and does not generate any extreme acid environment during the degradation of it contrary to PLGA. As such, PCL undergoes a degradation in two steps: first of all, hydrolytic degradation until a decrease in the molar mass to 3,000 g.mol-1; then intracellular degradation which occurs after phagocytosis of the small fragments of PCL. The ligament prosthesis according to the invention is a biodegradable and "biointegrable" artificial ligament which makes it possible to take away all the apprehensions and uncertainties due to non-degradable synthetic supports. It is a prosthetic structure inspired by and similar to the native tissue, biodegradable while still being sterilisable. It can optionally be seeded in order to facilitate the formation of functional tissues with controlled cell and tissue activity, having the required mechanical properties.

The prosthesis according to the invention is slowly resorbable in order to be gradually replaced with a functional tissue identical to that of the native ligament.

According to a preferred embodiment of the invention, said biodegradable fibre has a diameter between 1 and 400 μm.

According to a preferred embodiment of the invention said fibre has a molar mass between 1 and 200,000 g/mol.

According to a preferred embodiment of the invention, said layer is totally comprised of PCL fibres.

According to another preferred embodiment of the invention, said biodegradable fibres are rendered biologically active by grafting a polymer. As such, said biodegradable fibres comprise biologically active polymers.

According again to a preferred embodiment of the invention, said biologically active polymer is poly(styrene sodium sulfonate). As such, the ligament prosthesis according to the invention is conductive to the adhesion, proliferation, colonisation and cellular differentiation as well as to the production of an extracellular matrix in order to recreate a functional tissue.

In order to ensure good fibroblastic "repopulation" of the prostheses according to the invention, this invention propose a method for the biomimetic functionalisation of said prostheses, method conferring on them in particular the capacity to mimic living materials in order to improve their biological integration.

As such, this invention also relates to a method for treating artificial prostheses made of biodegradable fibres, in order to provide them with the capacity to mimic living materials, said method of biomimetic functionalisation being notable in that it comprises at least one step of grafting biologically active polymers or copolymers to the surface of the fibre of said prostheses, said step of grafting consists in carrying out a peroxidation of the surface par ozonation followed by a radical polymerisation with a solution of at least one monomer.

According to a preferred embodiment of the invention, the duration of ozonation for an ozone content of about 50 g/cm$^3$ is between 5 and 90 min.

According to another preferred embodiment of the invention, the monomer is styrene sodium sulfonate.

According again to a preferred embodiment of the invention, the solution of monomers has a concentration in monomer(s) between 5% and k %, where k is a concentration close to the solubility limit of the monomer(s) in the solution.

According to another preferred embodiment of the invention, the step of grafting is preceded by an additional step of preparing the surface of the fibre in a solvent medium able to modify the surface via swelling only, or in a solvent medium then in an aqueous medium.

According to another preferred embodiment of the invention, the solvent medium is comprised of ethyl ether, DMSO, hexane and/or ethyl ether.

In the case of PCL fibres, the solvent medium is advantageously constituted of ethyl ether.

According to another preferred embodiment of the invention, the solvent medium is constituted by at least one solvent able to modify the surface via swelling.

According to another preferred embodiment of the invention, the solvent able to modify the surface by swelling is of the cyclic ether or aliphatic type having low or zero toxicity.

According to another preferred embodiment of the invention, the solvent able to modify the surface by swelling is selected from the following group of solvents: tetrahydrofuran (THF), dimethylsulfoxide (DMSO), N,N-dimethylformamide (DMF), N,N-dimethylacetamide (DMA), N-methylpyrrolidone (NMP).

According to another preferred embodiment of the invention, the step of preparing the surface in an aqueous medium consists in hot-treating the polyester surface with an aqueous solution of alkaline or alkaline earth metal carbonate salts, such as for example $Na_2CO_3$ or $CaCO_3$, in order to eliminate the manufacturing residue of the polyester present on its surface.

According to another preferred embodiment of the invention said method comprises an additional step of impregnation of the prosthesis after the step of grafting by one or several biochemical agents that favour colonisation by fibroblasts.

According finally to another preferred embodiment of the invention, the biochemical agent is a protein from the family of fibronectins and/or type I and/or III collagen.

The method according to the invention is here applied to ligament prostheses that are already formed or to layers comprising biodegradable fibres that are part of the manufacture of said prostheses.

Other advantages and characteristics shall appear better in the following description of the full alternate embodiment, given by way of non-limiting example, of the ligament and of the method according to the invention.

DESCRIPTION OF EMBODIMENTS

Elaboration of Biodegradable Layers Made of PCL

PCL fibres can preferentially be obtained by extrusion and in particular by blow-moulding extrusion, extrusion casting and/or extrusion spinning.

The biodegradable fibres of PCL can moreover be obtained by the technique referred to as "electrospinning" that makes it possible to obtain fibres from a polymer solution and finally layers of polycaprolactone (PCL). The principle of this technique resides in the application of a high voltage on a polymer solution that then generates the forming of a stream that, once deposited on a collector, forms a fibrous mat. The versatility of this technique makes it possible to manufacture fibrous structures of which the diameter of the fibres is adjusted by influencing the concentration, composition and flow rate of the solution.

Step 1: Preparing the Surface of PCL

1A) In Solvent Medium:

This step referred to as scouring is necessary in order to eliminate the fats and impurities incorporated during the manufacture of the weft of PCL used as a structure for the ligament. It also makes it possible to prevent pathological reactions of the acute synovitis type during implantation in the patient. Furthermore, this step makes it possible to ensure growth of the fibroblasts on this PCL surface cleaned as such, growth that is not observed on surfaces that are not cleaned.

Three alternatives of this preparation in the solvent medium can be distinguished, according to the nature of the solvent and/or of the surfactant selected.

Alternative 1: Scouring with a solvent able to swell the surface made of PCL:

The use of a solvent able to swell the surface of the PCL offers the advantage of improving the grafting by increasing the number of peroxides on the surface treated during the step of ozonation.

Furthermore, it will be selected from the following group of solvents: tetrahydrofuran (THF), chloroform and dichloromethane. These solvents have the advantage of having a low or zero toxicity and as such allow for easy use in an industrial environment.

The treatment is carried out by immersion of the PCL into the solvent for a duration of about 5 minutes to about one hour, more preferably for 10 to 25 minutes.

As such, by way of example, a duration of 15 minutes at ambient temperature will be chosen for an immersion in tetrahydrofuran (THF)

Alternative 2: Scouring with a solvent and a surfactant.

This scouring is preferably carried out in the presence of hexane at a temperature below 60° C.

Alternative 3: Scouring without swelling of the surface:

A minimum of 12 extraction cycles is applied in a SOHXLET device and a control of the fatty body residue after the 12th cleaning cycle with hexane. These hexane cleaning cycles are followed by washing cycles with ethyl ether (RPE), minimum three washings with a residue control after the third washing.

1B) In Aqueous Medium:

The purpose of this optional step of preparing the surface in an aqueous medium is to remove the manufacturing residue of the PCL present on its surface. A surface that is perfectly primed before ozonation is as such obtained.

The treatment consists in washing the PCL in a solution of sodium carbonate ($Na_2CO_3$) at 5% by weight in distilled water. This washing is carried out hot, i.e. at above 60° C. and below 120° C. and more preferably with slight boiling, i.e. 100° C.±5° C., for approximately ten minutes. Of course, any other alkaline or alkaline earth metal carbonate such as $K_2CO_3$ or $CaCO_3$ can be used. The washing is followed by successive rinsings with distilled water until the pH of the rinsing water has returned to 7.

1C) Cleaning:

Regardless of the steps carried out hereinabove (alternative 1 or 2 of the step 1A, then the step 1B, or only the step 1A), the product made of PCL is then cleaned, for example by rinsing with absolute ethanol or with tetrahydrofuran (THF) followed by drying in an oven for a duration of 30 minutes, for example.

Step 2: Grafting of Biologically Active Polymers or Copolymers on the Surface Made from PCL:

2A) Choice and Preparation of the Monomers:

The monomers used according to the invention are monomers susceptible for polymerisation and radical copolymerisation giving rise to bio-compatible polymers that stimulate the proliferation and the cellular differentiation and plus particularly that of the fibroblasts. Such monomers containing hydroxyl, carboxylate, phosphonate, sulfonate and sulphate groups are, for example, described in U.S. Pat. No. 6,365,692 and can be used according to the invention alone or in a mixture thereof. It is possible, for example, to use methacrylic acid and styrene sulfonate, as well as mixtures thereof. Before using them for polymerisation, these monomers will be purified beforehand. As such for example, for styrene sulfonate sodium, it is purified by recrystallisation in a double-distilled water/alcohol mixture (10/90,v:v), then it is dissolved at 70° C. in this solution. It is then vacuum filtered with a sintered-glass disc with a porosity index of 3 and it is kept at 4° C. The sodium sulphonate crystals formed are recovered via filtration and the solid obtained is vacuum dried at 50° C. until a constant weight is obtained.

2B) Ozonation:

Prostheses or the wefts of PCL that constitute these prostheses treated beforehand according to step 1 are introduced into ozonation device such as used conventionally.

For example, a 500 $cm^3$ tubular reactor containing 100 $cm^3$ of double-distilled water can be used, said reactor is provided with a dip tube for the supply of ozone. It is possible, for example, to use an ozone gas flow equivalent to 50 $g/m^3$ of oxygen. For such a quantity of ozone, the optimum duration of ozonation of the PCL is from 5 to 90 minutes. The measurements of the peroxide content show that the optimum rate is obtained between 10 and 30 minutes of ozonation, still for this same flow of ozone. Also note that a duration of ozonation exceeding 90 minutes substantially degrades the surface make of PCL.

Note moreover the addition of the alternative 2 of the step 1A. Indeed, using a solvent able to swell the surface increases the peroxide content by a factor of 5, in relation to using a solvent without swelling. Once ozonation is complete, the prostheses or wefts made of PCL introduced into the ozonation device are rinsed and cleaned, for example according to the following protocol: rinsing three times with double-distilled water, then three times with absolute alcohol. Then, drying in the vacuum oven for 30 minutes at 25° C.

2C) Polymerisation:

The monomer or monomers selected and prepared according to the step 2A are placed in solution in water, more preferably double-distilled. Any combination can be selected that is compatible with the implementing of the radical polymerisation reaction with a minimum of 2% by weight. Advantageously concentrations close to the solubility limit of the monomer or monomers in the solution shall be chosen, with a viscous medium that as such favours the reactions of radical polymeric propagation in relation to termination reactions. This reverts to choosing a concentration by weight k=s−ε, where s is the solubility limit and ε is 1 to 7% by weight. As such for example, in the case of polystyrene sulfonate for which the solubility limit is 20% by weight, a concentration of 15% shall be chosen.

The duration of the step of polymerisation depends on the nature of the monomer. It is estimated as the time required for gelling of the medium at the reaction temperature. As such, for example, retain for polystyrene sulfonate that at 50° C., the polymerisation will last 1 hour and that at 30° C., it will last 15 hours.

The polymerisation reaction is conducted in a hermetically sealed enclosure and free of any oxygen, for example, by carrying out bubbling with argon. Into this enclosure is introduced the solution of monomers or of comonomers that is sought to be reacted and the prostheses or strips of tissue of PCL ozoned beforehand. The hermetically sealed recipient is heated in the water bath at the temperature and for the duration determined as mentioned hereinabove.

At the end of the reaction, the elements made of PCL that were grafted are extracted from the reactor. These grafted materials can then be washed in order to remove in particular residue of monomer(s) that did not react. For example, the functionalised surface can be washed several times with a suitable solvent of the monomer or monomers, with double-distilled water for example, and the washing can optionally be finished with any suitable solvent, absolute ethanol for example, in order to remove any traces of non-grafted monomers and polymers.

Step 3: Impregnation with Biochemical Agents:

This step is optional. It aims to reinforce the capacity of biological integration of the ligament to which was previously grafted biomimetic polymers such as disclosed in steps 1 and 2. As such, the impregnation of the prosthesis by one or several biochemical agents aims to increase these properties of adherence and of cellular proliferation. These biochemical agents favouring colonisation by fibroblasts are a protein of the family of fibronectins and/or type I and/or III collagen. A mixture of the preceding proteins will be used advantageously, i.e. a mixture of fibronectins and type I and/or III collagen: a synergetic effect is observed on the adherence of the fibroblasts. The impregnation of the prosthesis by these agents can, for example, be carried out by soaking in a bath containing collagen.

It goes without saying that this step of impregnation does not necessarily follow the step of grafting and that it can be inserted and be interleaved between other steps of preparing the ligament according to its stage of manufacture. Furthermore, this step of impregnation will be advantageously followed by a step of sterilisation of the ligament.

Sterilisation of Layers and Ligaments of PCL

The choice of the method of sterilisation is crucial during the development of biomaterials with a hydrolysable polyester base and special attention must be given to this. As aliphatic polyesters are sensitive to humidity and to heat, the methods of sterilisation by autoclave or dry heat cannot be considered. Furthermore, in this mode of sterilisation, are added the problems of toxicity linked to the difficulty in fully eliminating the residue of ethylene oxide from the biodegradable scaffold.

Three methods of sterilisation are preferably used: sterilisation with ethanol, UV radiation and beta radiation.

The invention claimed is:

1. An artificial ligament prosthesis comprising:
a surface layer consisting of biodegradable and resorbable fibres onto which a bio-active polymer or copolymer has been grafted, wherein each of said biodegradable and resorbable fibres has a diameter between 1 and 400 μm and consists of a material selected from a group consisting of poly ε-caprolactone (PCL), copolymers of PCL and of lactic acid (L and D), or of glycolic acid, copolymers of glycolic and lactic acids (L and D), polydioxanone, polyhydroxyalcanoate, and copolymers of polydioxanone and polyhydroxyalcanoate.

2. The artificial ligament prosthesis of claim 1, wherein said biodegradable and resorbable fibres consist of PCL.

3. The artificial ligament prosthesis of claim 1, wherein said bio-active polymer is poly(styrene sodium sulfonate).

4. The artificial ligament prosthesis of claim 3, wherein said artificial ligament is an articular or periarticular ligament.

5. The artificial ligament prosthesis of claim 4, wherein said artificial ligament is an anterior or posterior cruciate ligament.

6. A method for treating the artificial ligament prosthesis of claim 1, comprising:
grafting a bio-active polymer or copolymer onto biodegradable and resorbable fibres included on a surface of said prosthesis, wherein said grafting step comprises carrying out a peroxidation of the surface by ozonation followed by a radical polymerisation with a solution of at least one monomer.

7. The method of claim 6, wherein a duration of ozonation using an ozone content of about 50 g/cm$^3$ is between 5 and 90 minutes.

8. The method of claim 6, wherein the monomer is styrene sodium sulfonate.

9. The method of claim 6, wherein the solution of at least one monomer has a concentration in monomer(s) between 5% and k %, where k is a concentration close to the solubility limit of the monomer(s) in the solution.

10. The method of claim 6, wherein the grafting step is preceded by an additional step of preparing the surface in a solvent medium only, or preparing the surface in a solvent medium followed by an aqueous medium.

11. The method of claim 10, wherein the solvent medium comprises hexane or ethyl ether.

12. The method of claim 10, wherein the solvent medium comprises at least one solvent able to modify the surface via swelling.

13. The method of claim 12, wherein the solvent able to modify the surface via swelling is tetrahydrofuran (THF).

14. The method of claim 12, wherein the solvent able to modify the surface via swelling is selected from the following group of solvents: tetrahydrofuran (THF), dimethylsulfoxide (DMSO), N,N-dimethylformamide (DMF), N,N-dimethylacetamide (DMA), N-methylpyrrolidone (NMP).

15. The method of claim 10, wherein the step of preparing the surface in an aqueous medium comprises hot-treating the surface with an aqueous solution of alkaline or alkaline earth metal carbonate salts.

16. The method of claim 6, further comprising an additional step of impregnating the prosthesis, after the grafting step, by at least one biochemical agent that favors colonization of fibroblasts.

17. The method of claim 16, wherein the biochemical agent is a protein of the family of fibronectins and/or type I and/or III collagen.

\* \* \* \* \*